US008624465B2

(12) United States Patent
Do et al.

(10) Patent No.: US 8,624,465 B2
(45) Date of Patent: Jan. 7, 2014

(54) SURFACE ACOUSTIC WAVE SENSOR SYSTEM AND MEASUREMENT METHOD USING MULTIPLE-TRANSIT-ECHO WAVE

(75) Inventors: Jae Phil Do, Seoul (KR); Sang Kyu Kim, Yongin-si (KR); Jae Young Kim, Seoul (KR); Woo Chang Lee, Anyang-si (KR); Jae Yeon Jung, Hwaseong-si (KR); Soo Suk Lee, Suwon-si (KR); Youn Suk Choi, Gyeonggi-do (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 163 days.

(21) Appl. No.: 13/287,518

(22) Filed: Nov. 2, 2011

(65) Prior Publication Data
US 2013/0009517 A1 Jan. 10, 2013

(30) Foreign Application Priority Data
Jul. 8, 2011 (KR) .................. 10-2011-0068116

(51) Int. Cl.
*H03H 9/25* (2006.01)
*H01L 41/107* (2006.01)

(52) U.S. Cl.
USPC ....................................... 310/313 R; 310/338

(58) Field of Classification Search
USPC ............................................. 310/313 R, 338
See application file for complete search history.

(56) References Cited

U.S. PATENT DOCUMENTS

| 4,598,224 A * | 7/1986 | Ballato ................. 310/313 R |
| 4,726,225 A * | 2/1988 | Brace et al. ............. 73/204.23 |
| 4,736,128 A * | 4/1988 | Takoshima et al. ...... 310/313 R |
| 5,076,094 A * | 12/1991 | Frye et al. ................ 73/19.03 |
| 5,221,871 A * | 6/1993 | Fuchs et al. ............ 310/313 R |
| 6,029,500 A * | 2/2000 | Tom ......................... 73/31.05 |
| 6,906,451 B2 * | 6/2005 | Yamada et al. ............. 310/324 |
| 6,914,279 B2 * | 7/2005 | Lu et al. ...................... 506/39 |
| 7,608,978 B2 * | 10/2009 | Edmonson et al. ...... 310/313 R |
| 2007/0068256 A1 * | 3/2007 | Xu et al. ....................... 73/597 |

FOREIGN PATENT DOCUMENTS

| JP | 01-305318 | * | 8/1989 | ............. G01D 5/48 |
| KR | 1020100062065 | | 6/2010 | |
| KR | 1020100082956 | | 7/2010 | |
| WO | 2005066622 | | 7/2005 | |

* cited by examiner

*Primary Examiner* — Thomas Dougherty
(74) *Attorney, Agent, or Firm* — Leydig, Voit & Mayer, Ltd.

(57) ABSTRACT

A surface acoustic wave ("SAW") sensor system comprises a signal generating part, which applies an electrical signal to a SAW sensor, the SAW sensor connected to the signal generating part, which converts the electrical signal into a SAW, senses a measurement target using the SAW, and converts a SAW output corresponding to the measurement target into an electrical signal, and a signal measuring part connected to one side of the SAW sensor, which detects a change in the electrical signal by time-gating a multiple-transit-echo wave.

26 Claims, 3 Drawing Sheets

SURFACE ACOUSTIC WAVE SENSOR SYSTEM AND MEASUREMENT METHOD USING MULTIPLE-TRANSIT-ECHO WAVE

CROSS-REFERENCE TO RELATED APPLICATION

This application claims priority to Korean Patent Application No. 10-2011-0068116, filed on Jul. 8, 2011, and all the benefits accruing therefrom under 35 U.S.C. §119, the content of which in its entirety is herein incorporated by reference.

BACKGROUND

1. Field

Provided are a surface acoustic wave ("SAW") sensor system having substantially high sensitivity and integration, and a measurement method using a multiple-transit-echo wave.

2. Description of the Related Art

A SAW sensor refers to an element or a device for detecting or measuring an absolute value of a physical quantity or a chemical quantity, a change in physical quantity or chemical quantity, or intensity of a sound, light, or a radio wave from a target using a base and surface sensing technique and a SAW, and for converting them into an electrical signal.

SAW sensors are classified according to types of targets. For example, the SAW sensors may include a bio sensor for detecting protein, deoxyribonucleic acid ("DNA"), a virus, a bacterium, a cell, a tissue, and the like, a gas sensor for detecting toxic gas, inflammable gas, and the like, a temperature sensor for detecting temperature, a pressure sensor for detecting pressure, and a humidity sensor for detecting humidity. The SAW sensor may be used in various industrial fields.

SUMMARY

Provided are a surface acoustic wave ("SAW") sensor system having substantially high sensitivity and integration, and a measurement method using a multiple-transit-echo wave.

In an embodiment, a SAW sensor system comprises signal generating part providing a first electrical signal to a SAW sensor, wherein the SAW sensor connected to the signal generating part is adapted to convert the first electrical signal into a SAW, output a SAW corresponding to a measurement target when the measurement target contacts a sensing area, and convert the SAW corresponding to the measurement target into a second electrical signal; and a signal measuring part connected to one side of the SAW sensor and detecting a change in the second electrical signal by time-gating a multiple-transit-echo wave.

The SAW sensor may include a piezoelectric substrate, and an input part disposed on one side of the piezoelectric substrate and converting the first electrical signal into the SAW.

The SAW sensor may further include a sensing part and an output part, wherein the sensing part is disposed on the piezoelectric substrate, and the sensing part outputs the SAW corresponding to the measurement target so as to sense the measurement target, and wherein the output part is disposed on another side of the piezoelectric substrate and converts the SAW corresponding to the measurement target into the second electrical signal in the output part.

In another embodiment, A SAW sensor system comprises a SAW sensor; and a signal measuring part, wherein the SAW sensor includes an input part, an output part and a sensing part disposed between the input part and the output part, wherein a SAW from the input part is reflected by a portion of the output part and a first reflected SAW moves toward the input part, wherein the first reflected SAW is further reflected by a portion of the input part and a second reflected SAW moves toward the output part, wherein the second reflected SAW is a N multiple-transit-echo wave with N being three, wherein the output part converts the second reflected SAW into an electrical signal, and wherein the signal measuring part connected to the SAW sensor detects change in the electrical signal by time-gathering the N multiple-transit-echo wave with N being three.

In another embodiment, A measurement method using a multiple-transit-echo wave comprises converting a first electrical signal into a SAW, sensing a target using the SAW, outputting a SAW corresponding to the sensed target, converting the SAW corresponding to the target into a second electrical signal, and detecting a change in the second electrical signal by time-gating the multiple-transit-echo wave.

According to a measurement method using a multiple-transit-echo wave, sensitivity and integration of a SAW sensor is substantially improved. Thus, the manufacturing cost of the SAW sensor may be significantly reduced because the improved integration needs a less substrate area for the same number of elements.

BRIEF DESCRIPTION OF THE DRAWINGS

The above and other embodiments, advantages and features of this invention will become more apparent by describing in further detail exemplary embodiments thereof with reference to the accompanying drawings, in which.

DETAILED DESCRIPTION

The invention now will be described more fully hereinafter with reference to the accompanying drawings, in which a non-limiting embodiment is shown. This invention may, however, be embodied in many different forms, and should not be construed as limited to the example embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

One or more embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the claims.

Hereinafter, embodiments of the invention will be described in further detail with reference to the accompanying drawings.

Surface Acoustic Wave

As used herein, the term "surface acoustic wave ("SAW")" typically refers to a mechanical wave motion rather than an electromagnetic wave, which is generated from movement of particles due to various causes such as external thermal, mechanical, or electrical forces. The SAW typically includes vibration energy concentrated on a surface of an elastic body, and it is propagated along the surface of a solid as an earthquake is propagated along the ground.

A wave propagated through a medium is typically divided into three different components that are a longitudinal wave, a transversal wave and a surface wave. The longitudinal wave is a wave whose moving direction is substantially parallel to the displacement direction of particles. On the other hand, the moving direction of the transversal wave is substantially perpendicular to the displacement direction of particles. The surface wave occurs due to the combination of vectors of the longitudinal wave and the transversal wave.

Generally, about 90 percent (%) or more of a longitudinal displacement component and a transversal displacement component vanishes within a length of one wavelength from a material surface, and most energy thereof is concentrated within the length of one wavelength from the surface. Thus, the SAW is also called a transversal wave or a Rayleigh wave.

SAWs are typically classified into shear horizontal SAWs ("SH SAWs") and surface transverse waves ("STWs") according to types and classified into flexural plate waves ("FPWs"), Love waves, surface skimming bulk waves, and Lamb waves according to a purpose of use, for example, but is not limited thereto. Among these, the Lamb wave is mainly used for sensing a gas, and the Love wave is mainly used for sensing a liquid, for example.

SAW Sensor System

According to an embodiment, a SAW sensor system having high sensitivity and integration using a multiple-transit-echo wave is provided. The SAW sensor system may include a signal generating part, a SAW sensor which is connected to the signal generating part, and a signal measuring part which is connected to the SAW sensor.

As used herein, the term "sensitivity" refers to a degree of change in an output signal of a sensor with respect to a target.

As used herein, the term "integration" refers to a number of SAW sensors on one substrate with a predetermined area.

According to an embodiment, the sensitivity of the SAW sensor system may be substantially improved using a multiple-transit-echo wave.

As used herein, the term "signal generating part" refers to a region (or a component) which provides an electrical signal into the SAW sensor.

In one exemplary embodiment, the signal generating part may employ an oscillation technique which applies an output signal from the SAW sensor back to an input signal to the SAW sensor, for example. In a case of using a plurality of SAW sensors, each of the plurality of the SAW sensors may be oscillated independently, but is not limited thereto. Alternatively, a signal having a specific frequency may be applied to the SAW sensor using a network analyzer from outside of the SAW sensor.

As used herein, the term "SAW sensor" refers to a device for sensing presence and absence or a physical property and/or a chemical property of the target using the SAW.

The SAW sensor may convert an electrical signal into a SAW, and sense the target on a sensing area by using the SAW, and then convert a SAW output corresponding to the target into an electrical signal.

Figure 1:
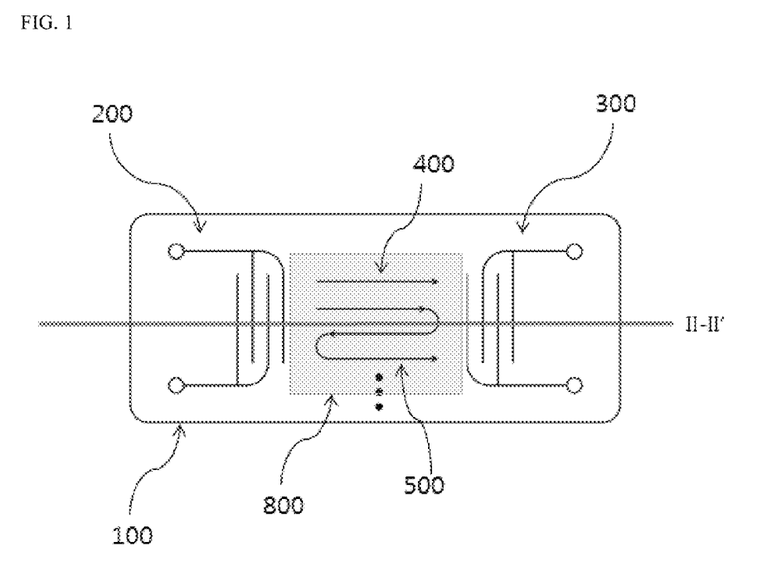
FIG. 1 is a diagram of an embodiment of a SAW sensor.
Figure 2:
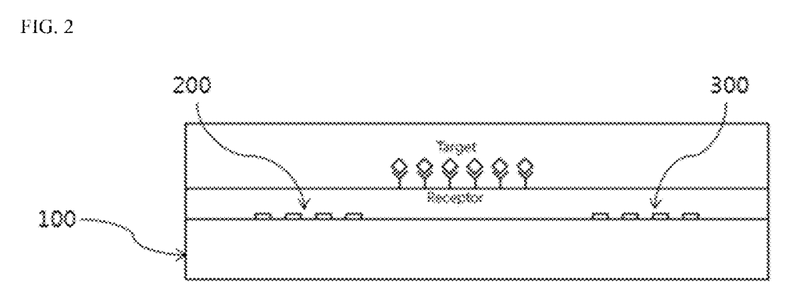
FIG. 2 is a cross-sectional view of the embodiment of the SAW sensor of FIG. 1 along a line II-IF.

The SAW sensor may include a piezoelectric substrate and an input part. An exemplary embodiment of the SAW sensor is shown in FIGS. 1 and 2.

As used herein, "piezoelectric substrate 100" refers to a substrate including a piezoelectric material.

The piezoelectric material has an electrical characteristic that is changed when a mechanical signal is applied (i.e., piezoelectric effect). Conversely, a mechanical signal is generated when an electrical signal is applied (i.e., the reverse piezoelectric effect). The piezoelectric material may include a metallic oxide or an insulating material, but is not limited thereto.

The piezoelectric material may include a metallic oxide such as lithium niobate ($LiNbO_3$), lithium tantalate ($LiTaO_3$), lithium tetraborate ($Li_2B_4O_7$), barium titanate ($BaTiO_3$), lead zirconate titanate (PZT), zinc oxide (ZnO), gallium arsenide (GaAs), quartz and niobate, berlinite, topaz, tourmaline group materials, potassium niobate, lithium niobate, sodium tungstate, $Ba_2NaNb_5O_5$, $Pb_2KNb_5O_{15}$ or any combination thereof, but is not limited thereto.

The piezoelectric material may include a piezoelectric polymer or a copolymer or mixture including one or more piezoelectric polymers, but is not limited thereto. For example, the piezoelectric polymer may be poly-vinylidene fluoride, and a copolymer or mixture of poly-vinylidene fluoride may be also used. The copolymer may include a block copolymer, an alternating block copolymer, a random copolymer, a random block copolymer, a graft copolymer, a star block copolymer, or any combination thereof. A polymer that may be copolymerized with polyvinylidene fluoride may include polytrifluoroethylene, polytetrafluoroethylene, polyacrylamide, polyhexafluoropropylene, polyacrylic acid, poly-(N-isopropylacrylamide), polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, or any combination thereof. The copolymer may include an electrically insulating polymer, and may be rendered electrically conductive by adding an intrinsically conductive polymer or an electrically conductive filler to the respective polymer.

Further, the piezoelectric material may include a composite that contains a polymer blended with other piezoelectric polymers. The piezoelectric polymer may include a filler that displays a piezoelectric characteristic to form a piezoelectric composite. For example, the piezoelectric filler may include lithium niobate ($LiNbO_3$), lithium tantalate ($LiTaO_3$), lithium tetraborate ($Li_2B_4O_7$), barium titanate ($BaTiO_3$), lead zirconate ($PbZrO_3$), lead titanate ($PbTiO_3$), lead zirconate titanate (PZT), zinc oxide (ZnO), gallium arsenide (GaAs), quartz and niobate, berlinite, topaz, tourmaline group materials, potassium niobate, lithium niobate, sodium tungstate, $Ba_2NaNb_5O_5$, $Pb_2KNb_5O_{15}$, or any combinations thereof, but is not limited thereto.

In an exemplary embodiment, a 36° YX $LiTaO_3$ ("LT") substrate may be used.

As used herein, the term "input part 200" refers to an area which is disposed on one side of the piezoelectric substrate 100 for converting an electrical signal applied from the signal generating part into a SAW that is a mechanical signal.

In one exemplary embodiment, the input part 200 may include an interdigital transducer ("IDT"). The input part 200 may further include an electrode pad (not shown) for receiving an electrical signal from the signal generating part (not shown) which is disposed on one end of the input part 200.

In one exemplary embodiment, the input part 200 may be disposed by patterning a metallic material on the piezoelectric substrate 100 into a predetermined form. The metallic material may include a thin film metal such as an aluminum alloy, a copper alloy, or gold, for example, but is not limited thereto. In order to prevent corrosion of the metallic material due to exposure to atmosphere or moisture, a protective layer such as an anti-oxidation layer may be disposed on a surface of the metallic material.

For example, the metallic material may include aluminum or an aluminum alloy, and an aluminum oxide thin film disposed on the surface thereof. The aluminum alloy may include aluminum (Al) as a main component, and at least one of titanium (Ti), silicon (Si), chromium (Cr), tungsten (W), iron (Fe), nickel (Ni), cobalt (Co), lead (Pb), niobium (Nb), tantalum (Ta), zinc (Zn), vanadium (V), and any combination thereof. The aluminum oxide thin film may be an artificially or natively formed aluminum oxide.

Further, since the metallic material may operate in a solution, an insulating layer may be disposed on the piezoelectric substrate 100. The insulating film may be used to insulate the IDT electrode, and also used as a wave guide layer when Love wave is generated. The insulating layer and the wave guide layer may include a polymer such as a silicon oxide ($SiO_2$) layer, a silicon nitride ($Si_xN_y$) layer, a zinc oxide (ZnO) layer, parylene, poly methyl methacrylate (PMMA) or any combination thereof. In one exemplary embodiment, the silicon oxide layer may be used along as a single insulation layer configuration, or both the zinc oxide layer and the silicon oxide layer may be used as a multi insulation layers configuration, for example.

The SAW sensor may further include a sensing part 800 and an output part 300.

As used herein, the term "sensing part" is disposed on the piezoelectric substrate 100 and refers to an area capable of outputting the SAW corresponding to a target with the SAW provided from the input part 200 when the target contacts the area of the sensing part.

The sensing part 800 may be configured by a delay line between the input part 200 and the output part 300, and may include a film form or a cell form.

When the target is contacted to the surface of the sensing part, due to influence of various types of causes such as pressure, rotator force, shock, tensile force, gravity, mass, evaporation, biochemistry, temperature, humidity, freezing, viscosity, displacement, liquidity, light sensing, optic angle, acceleration, abrasion, contamination, for example, a SAW corresponding to the target may be generated, which is substantially different in frequency, phase, amplitude, or the number of clocks from that of a SAW sent from the input part 200.

The target may include protein, DNA, viruses, bacteria, cell, tissue, gas, temperature, humidity, for example, but is not limited thereto.

As used herein, the "output part 300" is disposed on one side of the piezoelectric substrate 100, and refers to an area capable of converting a mechanical signal into an electrical signal so as to analyze the SAW corresponding to the target which is output and received from the sensing part. In one exemplary embodiment, the output part 300 may be disposed at an opposite side to the input part 200 with the sensing part interposed therebetween.

The output part 300 may have a form which is similar (see FIGS. 1 and 2) to that of the input part 200 or modified (not shown) from the input part 200. The output part 300 may include an electrode pad (not shown) for outputting a signal to the signal measuring part which may be disposed on one end of the output part 300.

The output part 300 may be disposed by patterning a metallic material on the piezoelectric substrate 100 into a previously set form. The metallic material is substantially the same as in the input part 200.

In the embodiment, the SAW sensor may be classified according to types of the target. For example, the SAW sensor may include a bio sensor for detecting protein, DNA, a virus, a bacterium, a cell, a tissue, and the like, a gas sensor for detecting toxic gas, inflammable gas, and the like, a temperature sensor for detecting temperature, a pressure sensor of detecting pressure, and a humidity sensor of detecting humidity, but is not limited thereto.

As used herein, the term "signal measuring part" refers to an area capable of measuring a change in an electrical signal by time-gating the multiple-transit-echo wave, for example. The changed signal is detected in the output part 300. As used herein, the term "time gating" refers to a technique of selecting and measuring a specific wave which exists at regular time intervals in a generated wave. The signal measuring part may detect the target bound to the sensing part using the detected signal.

For example, when the target to be measured is contacted to the sensing part, the frequency, phase, amplitude, the number of clocks, or the like of the electrical signal are changed in the output part 300. Thus, the signal measuring part may detect the fact that the target is contacted to the sensing part, and may qualitatively or quantitatively analyze the target.

As used herein, the "multiple-transit-echo wave" refers to a wave formed such that the SAW from the input part 200 is reflected between the output part 300 and the input part 200. The multiple-transit-echo wave may be generated when a metallic thin film of the IDT that configures the input part 200 and the output part 300 cause discontinuities of impedance and load, and the SAW is reflected by fingers of the IDT. In one embodiment, the impedance has a fixed value during the wave propagation regardless of the number of transitions of the multiple-transit-echo wave, but is not limited thereto.

The multiple-transit-echo wave may include N multiple-transit-echo waves where N is an odd number and greater than three such as a triple-transit-echo wave or a quintuple-transit-echo wave, for example.

In the embodiment, in the case of the triple-transit-echo wave 500, the SAW from the input part 200 is reflected by the output part 300 and moves toward the input part 200, and reflected again by the input part 200 and moves back to the output part 300, and then reaches the output part 300 following a main wave 400. As shown in FIG. 1, since the triple-transit-echo wave 500 passes through the sensing part three times, influence of a medium on the triple-transit-echo wave is about three times the main wave 400 passing through the sensing part once, and a delay time is also about three times the main wave 400.

According to the embodiment, a change in an electrical signal may be measured by time-gating, for example, the multiple-transit-echo wave such as the triple-transit-echo wave or the quintuple-transit-echo wave other than the main wave 400.

When the multiple-transit-echo wave is used for the output signal, compared to when the main wave is used for the output signal, influence of a medium contact on the surface increases, and thus sensitivity of the SAW sensor may be further improved. Furthermore, since the output signal is proportional to the length of the delay line along which the SAW travels, in the case of time-gating the multiple-transit-echo wave, compared to the case of time-gating the main wave, substantially the same output signal may be implemented with a shorter length of the delay line. In one embodiment, the length of a delay line may be longer than one hundred times of the wavelength to have a substantially sufficient sensitivity, but is not limited thereto.

In an exemplary embodiment, the triple-transit-echo wave is time-gated and then measured.

In the embodiment, the signal measuring part may include an apparatus such as a network analyzer, a vector voltmeter, a frequency counter, a phase detector, or an oscilloscope, for example, but is not limited thereto. In an exemplary embodiment, the triple-transit-echo wave is time-gated using the network analyzer.

According to another embodiment, a measurement method using a multiple-transit-echo wave is provided. The method includes converting an electrical signal into a SAW, sensing a target using the SAW, outputting a SAW corresponding to the sensed target, converting the corresponding SAW into an electrical signal, and detecting a change in the electrical signal by time-gating a multiple-transit-echo wave part. The method may further include detecting the target.

First, the electrical signal is converted to the SAW which is a mechanical signal through the input IDT of the input part 200, for example.

A physical, chemical, or electrical reaction of the SAW may change when the sensing part is contacted to the target. For example, the frequency, phase, amplitude, the number of clocks, or the like of the output signal of the SAW may change.

The changed SAW is converted into the electrical signal through the output IDT of the output part 300, for example. If the target is contacted to the sensing part and thus the weight of the sensing part changes, the shear speed of the SAW excited by the input IDT may change.

Then, the multiple-transit-echo wave is time-gated, and a change in frequency, phase, amplitude, or the number of clocks of the electrical signal is measured. In this manner, it is possible to precisely detect a physical property of the target such as pressure, rotator force, shock, tensile force, gravity, mass, evaporation, biochemistry, temperature, humidity, freezing, viscosity, displacement, liquidity, light sensing, optic angle, acceleration, abrasion, or contamination, for example, but is not limited thereto. Further, it is possible to analyze the target qualitatively or quantitatively.

When the multiple-transit-echo wave is used for the output signal, compared to the case when the main wave is used for the output signal, the sensitivity of the SAW sensor may be further improved.

When the triple-transit-echo wave is used, the influence of medium contacting the surface on the output signal is theoretically about three times higher than that of the case using the main wave. Therefore, the sensitivity of the SAW sensor may be substantially improved about three times when the triple-transit-echo wave is used. Further, since influence of a medium contacting the surface on the quintuple-transit-echo wave may be five times higher than that of the case with the main wave, the sensitivity of the SAW sensor using the quintuple-transit-echo may be substantially improved about five times. However, it is not limited to the theory.

In the case of conducting measurement using the multiple-transit-echo wave, compared to the case of using the main wave, the output signal with a substantially same sensitivity may be obtained with a shorter length of the delay line.

For example, in the case of the triple-transit-echo wave, the length of the delay line may be reduced to about one-third (⅓) compared to the case of the main wave. Similarly, in the case of the quintuple-transit-echo wave, the length of the delay line may be reduced to about one-fifth (1/5).

According to the embodiment, an increased number of sensors may be integrated on the substrate of substantially the same size when the multiple-transit-echo wave is used in the SAW sensor for measuring, and thereby the manufacturing cost for each SAW sensor may be significantly reduced.

Hereinafter, the exemplary embodiments and experimental examples of the invention will be described in further detail. However, they are not intended to limit the scope of the invention.

EXAMPLE 1

Time Domain Measurement of SAW

Figure 3:
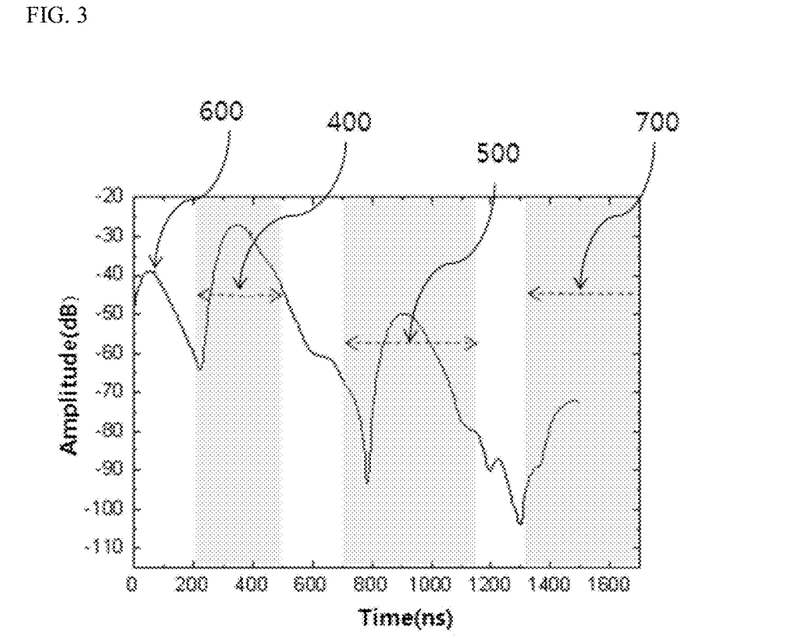
FIG. 3 is a graph illustrating a time domain of an embodiment of a SAW.

An electrical signal having a frequency of about 400 Megahertz (MHz) is applied to the SAW sensor shown in FIGS. 1 and 2 through a signal generator, and a time domain of an output SAW is measured. The result is shown in FIG. 3. The embodiment is demonstrated for example, and an electrical signal having any frequency may be applied to the SAW sensor. In one embodiment, an electrical single having a frequency up to about 1 Gigahertz (GHz) may be applied to the SAW sensor without a substantially large power loss.

Referring to FIG. 3, peaks sequentially appear on a time domain in order of an RF feed-through 600, the main wave 400, the triple-transit-echo wave 500, and the quintuple-transit-echo wave 700.

Since the traveling distance of the triple-transit-echo wave is three times longer than that of the main wave, the output signal of the triple-transit-echo wave has been influenced by the medium contacting the surface about three times more. Whereas the output signal of the quintuple-transit-echo wave has been influenced by the medium contacting the surface about five times more because the traveling distance of the quintuple-transit-echo wave is five times longer than that of the main wave.

EXAMPLE 2 phase Change of Main Wave and Triple-Transit-Echo Wave According to Concentration of Glycerol Glycerol diluted in distilled water is used as a target of the SAW sensor on a 36° YX LiTaO$_3$ ("LT") substrate, and a change in phase according to the concentration of glycerol is measured by the network analyzer (8753ES network analyzer commercially available from Agilent Technologies, Inc.). The result is shown in Table 1 and FIG. 4.

TABLE 1

| Glycerol (wt %) | 0 | 2 | 4 | 6 | 8 | 10 |
|---|---|---|---|---|---|---|
| Main wave | 0 | −55.5 | −56 | −57.2 | −57.8 | −58.3 |
| Triple-transit-echo wave | 0 | −159.8 | −160.9 | −162.5 | −164.6 | −166.7 |

Unit: degrees

Figure 4:
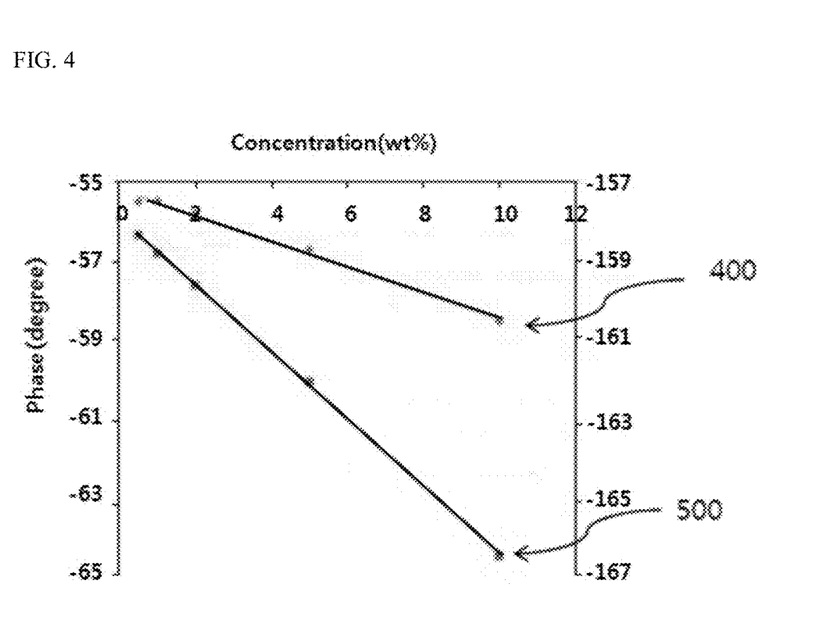
FIG. 4 is a graph illustrating an embodiment of a phase change of a main wave and a triple-transit-echo wave according to the concentration of glycerol.

Referring to Table 1 and FIG. 4, a change in phase measured by the main wave 400 according to the concentration of glycerol may be expressed by a function "−0.3236x−55.181" (where x is the concentration of glycerol), and a change in phase measured by the triple-transit-echo wave 500 according to the concentration of glycerol may be expressed by a function "−0.8443x−157.89" (where x is the concentration of glycerol).

Accordingly, the case of conducting phase change measurement using the triple-transit-echo wave, the sensitivity is substantially improved by about three times compared to the case of measuring the phase change using the main wave.

EXAMPLE 3

Amplitude Change of Main Wave and Triple-Transit-Echo Wave According to Concentration of Glycerol In the same manner as in Example 2, a change in amplitude of the SAW according to the concentration of glycerol is measured. The result is shown in Table 2 and FIG. 5.

TABLE 2

| Glycerol (wt %) | 0 | 2 | 4 | 6 | 8 | 10 |
|---|---|---|---|---|---|---|
| Main wave | 0 | −5.3 | −5.4 | −5.5 | −5.6 | −5.7 |
| Triple-transit-echo wave | 0 | −40.5 | −41.0 | −41.5 | −42.0 | −42.3 |

Unit: dB

Figure 5:
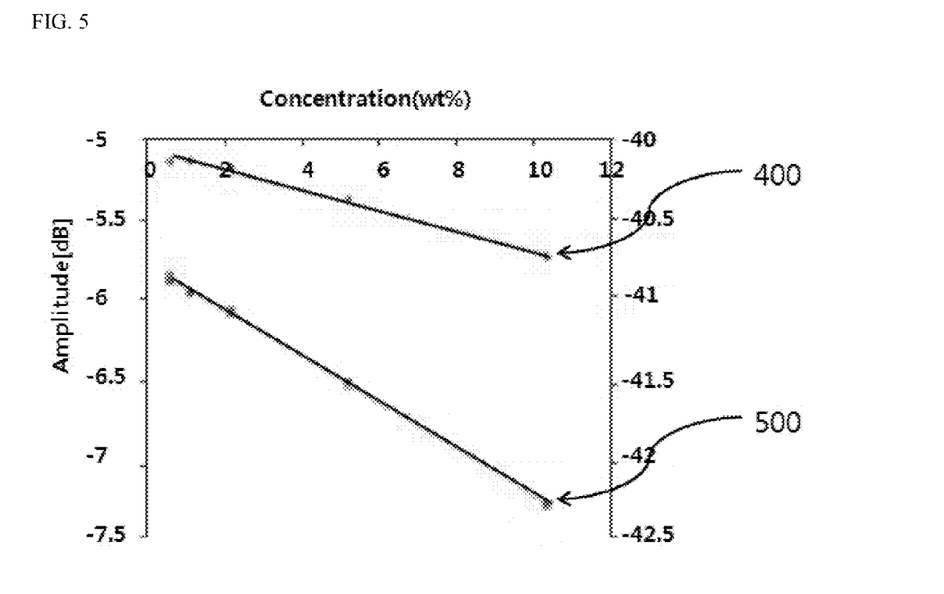
FIG. 5 is a graph illustrating an embodiment of an amplitude change of a main wave and a triple-transit-echo wave according to the concentration of glycerol.

Referring to Table 2 and FIG. 5, a change in amplitude measured by the main wave 400 according to the concentration of glycerol may be expressed by a function "−0.0627x−5.1054" (where x is the concentration of glycerol), and a change in amplitude measured by the triple-transit-echo wave 500 according to the concentration of glycerol may be expressed by a function "−0.1438x−40.794" (where x is the concentration of glycerol).

Accordingly, the case of conducting amplitude change measurement using the triple-transit-echo wave, the sensitivity is substantially improved by about three times compared to the case of measuring amplitude change using the main wave.

EXAMPLE 4

Phase Change of Surface Wave and Triple-Transit-Echo Wave According to Concentration of Troponin I In the same manner as in Example 2, a change in phase of a SAW according to the concentration of Troponin I inside a serum is measured. The result is shown in Table 3 and FIG. 6.

TABLE 3

|  | Troponin I (ng/mL) | | |
|---|---|---|---|
|  | 0.1 | 1 | 10 |
| Main wave | 0.5 | 5.3 | 21.4 |
| Triple-transit-echo wave | 12.6 | 25.7 | 78.6 |

Unit: degrees

Figure 6:
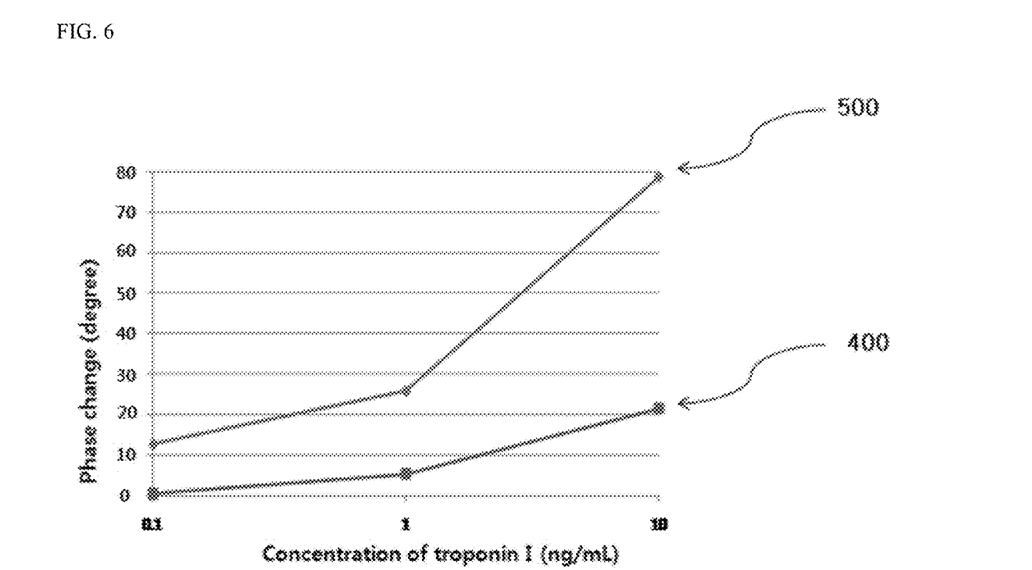
FIG. 6 is a graph illustrating an embodiment of a phase change of a main wave and a triple-transit-echo wave according to the concentration of Troponin I.

Referring to Table 3 and FIG. 6, it can be seen that a phase change measured using the triple-transit-echo wave 500 increases with respect to the concentration variation of Troponin I by about three times or more compared to the case of conducting measurement using the main wave.

From the results of the above examples, it can be seen that the sensitivity of the SAW sensor is substantially improved when the multiple-transit-echo wave is used, compared to the case of using the main wave. Therefore, the SAW sensor having substantially the same sensitivity may be designed with a shortened length of the delay line, which may significantly reduce the manufacturing cost and/or size of the sensor system because the shorter length of the delay line requires the less substrate area for each SAW sensor and integrates the increased number of SAW sensors within a predetermined substrate area.

While the invention has been particularly shown and described with reference to embodiments thereof, it will be understood by those of ordinary skill in the art that various changes in form and details may be made therein without departing from the spirit or scope of the invention as defined by the following claims

What is claimed is:

1. A surface acoustic wave (SAW) sensor system, comprising:
   a signal generating part providing a first electrical signal to a SAW sensor,
   wherein the SAW sensor connected to the signal generating part is adapted to convert the first electrical signal into a SAW, output a SAW corresponding to a measurement target when the measurement target contacts a sensing area, and convert the SAW corresponding to the measurement target into a second electrical signal;
   a receptor disposed on the sensing area and configured to receive the measurement target such that the measurement target is in contact with the sensing area; and
   a signal measuring part connected to one side of the SAW sensor and detecting a change in the second electrical signal by time-gating a multiple-transit-echo wave.

2. The SAW sensor system of claim 1, wherein the SAW sensor includes
   a piezoelectric substrate, and
   an input part disposed on one side of the piezoelectric substrate and converting the first electrical signal into the SAW.

3. The SAW sensor system of claim 2, wherein the SAW sensor further includes
   a sensing part and an output part,
   wherein the sensing part is disposed on the piezoelectric substrate, and the sensing part outputs the SAW corresponding to the measurement target so as to sense the measurement target, and
   wherein the output part is disposed on another side of the piezoelectric substrate and converts the SAW corresponding to the measurement target into the second electrical signal in the output part.

4. The SAW sensor system of claim 3, wherein the multiple-transit-echo wave is reflected by a portion of the output part at least one time, and
   wherein the multiple-transit-echo wave is further reflected by a portion of the input part at least one time.

5. The SAW sensor system of claim 2, further comprising:
   an anti-oxidation film disposed on the piezoelectric substrate.

6. The SAW sensor system of claim 2, further comprising:
   an insulating film disposed on the piezoelectric substrate.

7. The SAW sensor system of claim 3, wherein at least one of the input part and the output part includes an interdigital transducer ("IDT").

8. The SAW sensor system of claim 1, wherein the SAW is selected from a flexural plate wave, a Love wave, a surface skimming bulk wave and a Lamb wave.

9. The SAW sensor system of claim 1, wherein the measurement target is at least one of protein, DNA, a virus, bacteria, a cell, a tissue, gas, temperature, pressure and humidity.

10. The SAW sensor system of claim 1, wherein the SAW sensor is selected from a bio sensor, a gas sensor, a temperature sensor, a pressure sensor and a humidity sensor.

11. The SAW sensor system of claim 1, wherein the multiple-transit-echo wave is at least one of N multiple-transit-echo waves where N is an odd number and equal to or greater than 3.

12. The SAW sensor system of claim 1, wherein the signal measuring part detects a change in at least one of frequency, phase, amplitude, and the number of clocks of the electrical signal.

13. The SAW sensor system of claim 1, wherein the signal measuring part detects at least one of pressure, rotator force, shock, tensile force, gravity, mass, evaporation, biochemistry, temperature, humidity, freezing, viscosity, displacement, liquidity, light sensing, optic angle, acceleration, abrasion and contamination of the measurement target.

14. A surface acoustic wave (SAW) sensor system, comprising:
   a SAW sensor; and
   a signal measuring part,
   wherein the SAW sensor includes an input part, an output part and a sensing part disposed between the input part and the output part,
   wherein a receptor is disposed on a sensing area of the sensing part and configured to receive a measurement target such that the measurement target is in contact with the sensing area
   wherein a SAW from the input part is reflected by a portion of the output part and a first reflected SAW moves toward the input part,
   wherein the first reflected SAW is further reflected by a portion of the input part and a second reflected SAW moves toward the output part,
   wherein the second reflected SAW is a N multiple-transit-echo wave with N being three,
   wherein the output part converts the second reflected SAW into an electrical signal, and
   wherein the signal measuring part connected to the SAW sensor detects change in the electrical signal by time-gating the N multiple-transit-echo wave with N being three.

15. The SAW sensor system of claim 14, wherein the sensing part is disposed on a piezoelectric substrate.

16. The SAW sensor system of claim 15, further comprising an insulating film disposed on the piezoelectric substrate.

17. The SAW sensor system of claim 14, wherein at least one of the input part and the output part includes an interdigital transducer ("IDT").

18. The SAW sensor system of claim 14, wherein the signal measuring part detects a change in at least one of frequency, phase, amplitude, and the number of clocks of the electrical signal.

19. A measurement method using a multiple-transit-echo wave, comprising:
   receiving a target at a receptor disposed on a sensing area of a piezoelectric substrate of a SAW sensor system such that the target contacts the sensing area
   converting a first electrical signal into a SAW;
   sensing the target using the SAW;
   outputting a SAW corresponding to the sensed target;
   converting the SAW corresponding to the target into a second electrical signal; and
   detecting a change in the second electrical signal by time-gating the multiple-transit-echo wave.

20. The method of claim 19, wherein the SAW is selected from a flexural plate wave, a Love wave, a surface skimming bulk wave and a Lamb wave.

21. The method of claim 19, wherein the target is at least one of protein, DNA, a virus, bacteria, a cell, a tissue, gas, temperature, pressure and humidity.

22. The method of claim 19, wherein the multiple-transit-echo wave is at least one of N multiple-transit-echo waves where N is an odd number and equal to or greater than 3.

23. The method of claim 19, wherein the change in the second electrical signal is a change in at least one of frequency, phase, amplitude, and the number of clocks of the electrical signal.

24. The method of claim 19, further comprising detecting the target.

25. The method of claim 24, wherein detecting the target includes detecting at least one of pressure, rotator force, shock, tensile force, gravity, mass, evaporation, biochemistry, temperature, humidity, freezing, viscosity, displacement, liquidity, light sensing, optic angle, acceleration, abrasion, and contamination of the target.

26. The method of claim 19, wherein measurement using the multiple-transit-echo wave provides a higher sensitivity than measurement using a main wave.

* * * * *